United States Patent [19]

Takagi et al.

[11] 4,378,435

[45] Mar. 29, 1983

[54] PROCESS FOR PROVIDING ENZYME ACTIVITY TO A SOLID SURFACE

[75] Inventors: Kunihiko Takagi, Kyoto; Yasunori Yabushita, Yamatotakada, both of Japan

[73] Assignee: Unitika, Ltd., Hyogo, Japan

[21] Appl. No.: 200,657

[22] Filed: Oct. 27, 1980

[30] Foreign Application Priority Data

Oct. 27, 1979 [JP] Japan ................................ 54-139121

[51] Int. Cl.$^3$ .......................................... C12N 11/06
[52] U.S. Cl. .................................... 435/180; 435/215; 435/216; 427/2; 3/1.4; 3/1.5; 3/1.7; 604/64
[58] Field of Search .................. 435/180, 181, 23, 24, 435/215, 216

[56] References Cited

U.S. PATENT DOCUMENTS

| | | | |
|---|---|---|---|
| 3,649,457 | 3/1972 | Westman | 435/180 |
| 3,715,278 | 2/1973 | Miller | 435/181 |
| 3,764,477 | 10/1973 | Lehmann | 435/180 |
| 3,910,825 | 10/1975 | Heiper | 435/180 |
| 4,229,536 | 10/1980 | De Filippi | 435/181 |

FOREIGN PATENT DOCUMENTS 1274869  2/1970  United Kingdom ................ 435/181

*Primary Examiner*—Sam Silverberg
*Attorney, Agent, or Firm*—Sughrue, Mion, Zinn, Macpeak and Seas

[57] ABSTRACT

A process for providing enzyme activity to the surface of an article is described, comprising forming a film on the surface of the article, said film comprising an acid anhydride group-containing polymer and a polyol, wherein the acid anhydride groups are partially reacted with the polyol, and thereafter reacting the unreacted acid anhydride groups with an enzyme. Such an article provided with enzyme activity on the surface can be used for the production of food, medicines, etc., and as a medical material.

26 Claims, No Drawings

Patent text

PROCESS FOR PROVIDING ENZYME ACTIVITY TO A SOLID SURFACE

BACKGROUND OF THE INVENTION

This invention relates to a method for providing enzyme activity to the surface of an article.

Studies have been made on the use of enzymes bonded onto water-insoluble carriers as catalysts for the production of food, medicines, etc., and they have reportedly been put into practical use for the production of amino acid, fruit sugar, etc. Additionally, the use of a tube with urease, uricase, or the like fixed thereon as a material for clinical examinations, and the use of a tube with urokinase fixed thereon as an antithrombogenic medical material, have been studied.

Bonding such enzymes onto the surface of an article requires the presence on the surface of the article of active groups capable of bonding with the enzymes. Thus, various methods to introduce active groups into the surface of articles comprising cellulose, dextran, polyamide, polyester, polyvinyl alcohol, polyvinyl chloride, silicone rubber, etc., have been proposed. These methods, however, vary in their capability of bonding the enzymes, depending upon the material constituting the article, and, moreover, require very complicated surface treatments which sometimes deteriorate the mechanical properties of the article, making it impossible to increase the enzyme activity of the surface.

The inventors have filed in the United States the following two patent applications:

"A Process for Producing an Antithrombogenic Polyurethane by Fixation of a Fibrinolytic Enzyme to The Surface of Polyurethane" (U.S. patent application Ser. No. 928,496); and "Process for Producing Antithrombogenic Vinyl Acetate Polymer or Hydrolysate Thereof" (U.S. patent application Ser. No. 43,601).

SUMMARY OF THE INVENTION

The object of this invention is to provide a simplified method which facilitates the bonding of an enzyme on the surface of an article, irrespective of the type of the material constituting the article, and which furthermore enables the provision of high enzyme activity without deteriorating the mechanical properties of the article.

This invention, therefore, is a method for providing enzyme activity to the surface of an article, comprising forming a film on the surface of the article, said film comprising an acid anhydride group-containing polymer and a polyol, wherein the acid anhydride groups are partially reacted with the polyol, and thereafter reacting the unreacted acid anhydride groups of the film with an enzyme.

DETAILED DESCRIPTION OF THE INVENTION

Polymers containing acid anhydride groups which are useful in this invention include homo- and copolymers of $\alpha,\beta$-unsaturated carboxylic acid anhydrides such as maleic anhydride, acrylic anhydride, methacrylic anhydride, itaconic anhydride, methyl maleic anhydride, acrylic and methacrylic mixed anhydride, acrylic and propionic mixed anhydride, etc. Of these polymers, a copolymer of maleic anhydride, a homopolymer of acrylic anhydride and a homopolymer of methacrylic anhydride are preferred.

Comonomers which can be used in preparing maleic anhydride copolymers include ethylene, propylene, 1-butene, isobutylene, cis-butene-2, trans-butene-2, styrene, methyl vinyl ether, dodecyl vinyl ether, methyl methacrylate, allyl chloride, vinyl chloride, acrylonitrile, etc. Of maleic anhydride copolymers prepared using the above comonomers, a maleic anhydride-ethylene copolymer, a maleic anhydride-styrene copolymer and a maleic anhydride-methyl vinyl ether copolymer are available on the market and it is therefore advantageous to use these copolymers in this invention.

The molecular weight of acid anhydride group-containing polymers is typically from about 500 to 1,000,000, and preferably from about 1,000 to 500,000.

By the term "polyol" as used in this invention is meant a compound containing at least two hydroxyl groups. Examples of such polyols include diols such as ethylene glycol, diethylene glycol, propylene glycol, trimethylene glycol, butylene glycol, tetramethylene glycol, xylylene glycol, 1,4-bis(2-hydroxyethoxy)benzene, etc., triols such as glycerin, trimethylol propane, etc., tetraols such as erythritol, pentaerythritol, diglycerin, etc., pentaols such as arabitol, xylitol, fructose, glucose, etc., hexaols such as mannitol, sorbitol, etc., and so on. In addition, polyether-polyol and polyester-polyol can be used.

Suitable polyether-polyols which can be used include the reaction product formed between a polyol having from 2 to 20 carbon atoms and from 2 to 6 hydroxy groups, for example, diols such as ethylene glycol, propylene glycol, butylene glycol, etc., triols such as glycerol, trimethylol propane, etc., and tetraols such as pentaerythritol, etc., pentaols such as fructose, glucose, etc., and hexaols such as sorbitol, etc., and an alkylene oxide such as ethylene oxide, propylene oxide, butylene oxide or a mixture of ethylene oxide and propylene oxide.

Suitable polyester-polyols which can be used include those obtained by polycondensing a polyol with a polycarboxylic acid in such a manner that the terminals are substituted with hydroxyl groups. Examples of suitable polycarboxylic acids for preparing the polyester-polyol include those having from 2 to 20 carbon atoms and 2 to 4 carboxyl groups, for example, dicarboxylic acids such as oxalic acid, malonic acid, succinic acid, glutaric acid, adipic acid, sebacic acid, maleic acid, fumaric acid, isophthalic acid, terephthalic acid, etc., tricarboxylic acids such as trimellitic acid, etc., and tetracarboxylic acids such as pyromellitic acid and examples of suitable polyols include those having from 2 to 10 carbon atoms and from 2 to 4 hydroxy groups, for example, diols such as ethylene glycol, propylene glycol, butylene glycol, 1,6-hexanediol, etc., triols such as glycerol, trimethylol propane, etc., and tetraols such as pentaerythritol, etc. The polyester-polyol can also be prepared from a lactone such as caprolactone, $\beta$-propiolactone, $\alpha,\alpha$-dimethyl-$\beta$-propiolactone, $\alpha,\alpha$-bis-chloromethyl-$\beta$-propiolactone, etc.

The molecular weight of polyols as used in this invention is about 5,000 or less, and preferably about 3,000 or less.

The article as used in this invention can be in various shapes, depending upon the purpose for which it is used, including a bead, a film, a permeable membrane, a sheet, a tube, a hollow fiber, a fiber, a cloth, a sponge, etc.

Materials which can be used in preparing the article of this invention include metal materials such as iron, silver, lead, nickel, steel, copper, zinc, stainless steel, cobalt-nickel, tantalum, titanium, etc., inorganic materials such as glass, carbon, ceramics, asbestos, polyphosphagen, etc., and organic polymeric materials.

Examples of such organic polymeric materials include polymers of olefins such as ethylene, propylene, 1-butene, 1-pentene and isobutylene, polymers of halogenated olefins such as vinyl chloride, vinylidene chloride, trifluoroethylene and tetrafluoroethylene, polymers of aromatic vinyl compounds such as styrene, divinyl benzene, α-methylstyrene or vinylpyridine, polymers of dienes such as butadiene or isoprene, polymers of N-vinyl compounds such as N-vinylamine or N-vinylpyrrolidone, polyvinyl alcohol and the esters thereof such as polyvinyl alcohol acetate, polymers of vinyl ethers such as vinyl methyl ether and tetramethylene glycol divinyl ether, polymers of sulfur-containing vinyl compounds such as vinyl sulfone or vinyl sulfoxide, polymers of unsaturated aldehydes such as acrolein, polymers of unsaturated ketones such as methyl vinyl ketone, polymers of $\alpha,\beta$-unsaturated carboxylic acids such as acrylic acid, methacrylic acid, maleic acid or fumaric acid, polymers of $\alpha,\beta$-unsaturated carboxylic acid esters such as methyl acrylate, ethyl acrylate, methyl methacrylate, ethyl methacrylate or maleic acid monomethyl ester, polymers of $\alpha,\beta$-unsaturated nitriles such as acrylonitrile or methacrylonitrile, polymers of $\alpha,\beta$-unsaturated carboxylic acid amides such as acrylamide or methacrylamide, polyethers such as polyphenylene oxide, polymethylene oxide, polyethylene oxide or polytetramethylene oxide, polypeptides such as polyglutamic acid, polyalanine, polylysine, polyaspartic acid or polyphenylalanine, polyamides such as nylon-3, nylon-4, nylon-5, nylon-6, nylon-7, nylon-11, nylon-12, nylon-6,6, nylon-6,10, poly(m-phenyleneisophthalamide), or poly(p-phenyleneterephthalamide), polyesters derived from polycarboxylic acids such as terephthalic acid, isophthalic acid, adipic acid, maleic acid, fumaric acid, or trimellitic acid and polyols such as ethylene glycol, propylene glycol, butylene glycol, pentaerythritol or bisphenol A, polyesters derived from hydroxycarboxylic acids such as glycolic acid, lactic acid or hydroxypivalic acid, silicone rubbers such as dimethylpolysiloxane, methylphenylpolysiloxane, methylvinylpolysiloxane, cyanoalkylmethylpolysiloxanes, and fluoroalkylmethylpolysiloxanes, polyurethanes derived from polyisocyanates such as toluene diisocyanate, xylene diisocyanate, phenylene diisocyanate, ethylene diisocyanate, diphenylmethane diisocyanate and toluene triisocyanate and polyols such as polyethylene glycol, polypropylene glycol or polyesters containing a hydroxy group at both terminals, formaldehyde resins such as phenol-formaldehyde resins, xylene-formaldehyde resins, urea-formaldehyde resins, or melamine-formaldehyde resins, polymers containing a tetracyclic ring such as polyimides, polybenzimidazoles and polythiazoles, polycarbonates derived from bisphenol A and phosgene, polysulfones derived from bisphenol A and 4,4'-dichlorodiphenylsulfone, natural organic polymers such as cellulose, starch, proteins, and natural rubber.

In accordance with the method of this invention, a film comprising an acid anhydride group-containing polymer and a polyol, wherein the acid anhydride groups are partially reacted with the polyol, is first formed on the surface of the article (e.g., by conventional coating techniques). The simplest and most effective method of forming the film comprises coating a solution containing the acid anhydride group-containing polymer and polyol on the article, to form a film on the surface of the article, and then reacting the acid anhydride group-containing polymer and the polyol by heating.

Solvents which can be used in preparing the solution of the acid anhydride group-containing polymer and polyol include dioxane, tetrahydrofuran, ethyl acetate, methyl acetate, acetone, methyl ethyl ketone, chloroform, methylene chloride, nitromethane, nitropropane, benzene, toluene, xylene, dimethylformamide, dimethylacetamide, N-methylpyrrolidone, dimethylsulfoxide, ethylene glycol diethyl ether, ethylene glycol dimethyl ether, diethylene glycol dimethyl ether, diethylene glycol diethyl ether, anisole, phenetole, etc. These solvents can be used alone or in admixtures comprising two or more thereof.

The concentration of the acid anhydride group-containing polymer in the solution is preferably from about 0.005 to 20% by weight, and more preferably from 0.01 to 10% by weight, and the concentration of the polyol is preferably from about 0.01 to 30% by weight, and more preferably from 0.05 to 10% by weight.

In order to accelerate the reaction between the anhydride group and polyol, to this solution can be added, if desired, acids such as acetic acid, sulfuric acid, chloric acid, p-toluenesulfonic acid, etc., or bases such as triethylamine, pyridine, etc., so that the concentration of acids or bases be preferably about 0.001 to 2% by weight and more preferably about 0.005 to 1% by weight.

For coating the solution thus-prepared on the surface of the article, a method of soaking the article in the solution, a method of spraying the solution on the solid surface, a method of coating the solution by use of a doctor knife, a brush or the like, etc., can be used.

After the coating of the article with the solution, the article is dried to remove the solvent and it is then heated at a temperature of preferably from about 30° to 180° C., and more preferably from 50° to 150° C., for a period of preferably from about 5 minutes to 48 hours, and more preferably from 10 minutes to 24 hours, to cause the reaction between the acid anhydride group-containing polymer and the polyol.

The thickness of the film formed on the surface of the article is preferably from about $0.01\mu$ to $500\mu$, and more preferably from $0.05\mu$ to $100\mu$.

In the method of this invention, it is necessary to allow unreacted acid anhydride groups to remain in the coating film formed on the surface of the article. The simplest method to achieve the above object is to regulate the amounts of the acid anhydride group-containing polymer and polyol so that the molar ratio of the acid anhydride group to the hydroxy group be more than 1. Even though the molar ratio of the acid anhydride group to the hydroxy group is not more than 1, unreacted acid anhydride groups are allowed to remain by suitably adjusting the reaction temperature and reaction time.

Another method of forming the film on the surface of the article, said film comprising the acid anhydride group-containing polymer and the polyol and a part of the acid anhydride group being reacted with the polyol, comprises coating a solution of the acid anhydride group-containing polymer (the concentration is preferably about 0.005 to 20% by weight and especially preferably about 0.01 to 10% by weight) and then a solution of the polyol (the concentration is preferably about 0.01% by weight or more and especially preferably about 0.05% by weight or more, and when the polyol is liquid at room temperature, it can be used as is) or in the reverse order, on the surface of the article to form a film thereof, and thereafter reacting the acid anhydride group and polyol by heating.

Another method of forming the film on the surface of the article comprises coating a solution of the acid anhydride group-containing polymer or a solution of the polyol on the surface of the article, soaking the article in the solution of the polyol or the solution of the acid anhydride group-containing polymer and then reacting the acid anhydride group-containing polymer and the polyol by heating.

In the method of this invention, the unreacted acid anhydride group of the coating film and an enzyme are then reacted. The reaction between the unreacted acid anhydride group of the film and the enzyme can be carried out as follows: the enzyme is dissolved in water, methanol, ethanol, propanol, dioxane, dimethylformamide, dimethyl sulfoxide, etc., or a mixture thereof and the article is treated in the enzyme solution at a temperature of preferably from about −20° to 60° C., and especially preferably from 0° to 40° C., for a period of preferably from about 30 minutes to 7 days, and especially preferably from 1 hour to 3 days. The concentration of the enzyme is preferably from about 0.0001 to 50 mg/l, and especially preferably from 0.0005 to 10 mg/l. The treatment of the article with the enzyme solution is carried out by soaking the article in the enzyme solution. As necessary, a fresh surface of the article is provided by stirring, circulation, shaking, etc., during the surface treatment.

At this treatment, the pH of the enzyme solution is desirably maintained at from about 3 to 10 and preferably at from 4 to 9. For this purpose, buffers such as a phosphate buffer, an acetate buffer, etc., alkalis such as sodium hydroxide, etc., and acids such as hydrochloric acid, etc., can be used. Additionally, in order to stabilize the enzyme solution and prevent the inactivation of the enzyme, as additives, 10 g/l or less of proteins such as albumin and gelatin or 2 mol/l or less of salts such as sodium chloride can be, as necessary, added to the enzyme solution.

After the treatment of the article with the enzyme solution, the article is washed with water, a buffer, e.g., a phosphate buffer, an acetate buffer, etc., or a solution of a salt, e.g., sodium chloride. Thereafter, the article is stored in water or a solution of a salt, or alternatively after being dried, can be, as necessary, stored in an atmosphere of an inert gas, e.g., nitrogen, argon, etc., or in vacuo, or in atmosphere.

Almost all enzymes can be used in the method of this invention, including fibrinolytic enzymes. Useful enzymes include oxidoreductase such as alcohol dehydrogenase, lactate dehydrogenase, glucose-6-phosphate dehydrogenase, glucose oxidase, glyceraldehydephosphate dehydrogenase, luciferase, glutamate dehydrogenase, L-amino acid oxidase, tyrosinase, catalase, peroxidase, etc., transferase such as hexokinase, pyruvate kinase, creatine kinase, polynucleotide phosphorylase, ribonuclease, t-RNA nucleotidyltransferase, hydrolase such as lipase, acetylcholinesterase, cholinesterase, steroid esterase, alkaline phosphatase, acid phosphatase, fructose-1,6-diphosphatase, deoxyribonuclease, staphylococcal nuclease, sterol sulfatase, α-amylase, β-amylase, γ-amylase, cellulase, dextranase, β-glucosidase, invertase, β-glucuronidase, hyaluronidase, naringinase, leucine aminopeptidase, carboxypeptidase, prolidase, pepsin, rennin, trypsin, chymotrypsin, papain, ficin, thrombin, renin, subtilopeptidase, kallikrein, bromelain, pronase, streptokinase, urokinase, plasmin, brinolase, L-asparginase, urease, uricase, penicillin amidase, aminoacylase, ATPase, apyrase, etc., lyase such as pyruvate decarboxylase, fructosediphosphate aldolase, threonine deaminase, etc., isomerase such as glucose isomerase, etc., ligase such as isoleucyl t-RNA synthetase, etc. Using these enzymes, the corresponding enzyme activity can be provided to the surface of the article by the method of this invention.

The method of this invention has the advantage that it can be applied to any article whether it contains reactive functional groups in the surface thereof or not, without deteriorating the mechanical properties of the article. Furthermore, this invention has the advantages that the bonding strength between the article and enzyme is strong, the enzyme activity is high and the enzyme activity is maintained for a long period of time, and therefore that the continuous reaction is possible. For example, beads provided with enzyme activity by the method of this invention can be packed in a column and on flowing a substrate solution through the column, a reaction product can continuously be removed. Where the enzyme activity is provided on the inner walls of a tube, the reaction product can continuously be removed by passing the substrate solution through the tube. Furthermore, where the enzyme activity is provided to the surface of a membrane having selective permeability or to the surface of a hollow fiber, the enzyme reaction can be carried out while at the same time separating the substrate and the reaction product.

The article provided with the enzyme activity can be utilized for medical applications. For example, the provision of the fibrinolytic activity of a fibrinolytic enzyme, e.g., urokinase, streptokinase, brinolase, plasmin, etc., to tubes for catheter, surgical drain and extracarporeal circulation, tubes for vascular prosthesis, adsorbents for blood purification, heart assist devices, artificial hearts, artificial kidneys, artificial lungs, etc., which come in direct contact with blood permits the prevention of thrombus formation.

The following examples are given to illustrate this invention in greater detail.

EXAMPLE 1

A 200μ thick polyurethane film was soaked in an acetone solution of 1 (W/V)% of a maleic anhydridemethyl vinyl ether copolymer and 1 (W/V)% of polyethylene glycol having a molecular weight of 400 for 30 seconds at room temperature and then heated under reduced pressure at from 90° to 100° C. for 3 hours. Infrared analysis of the film confirmed that the surface of the film contained the acid anhydride group (1,840 cm$^{-1}$).

This film was soaked in a physiological saline solution (600 unit/ml) of urokinase at 7° C. for 24 hours and then washed well with a physiological saline solution. The polyurethane film with urokinase bonded thereto was cut to form a disk having a diameter of 5 mm, and by using a fibrin plate, the fibrinolytic activity of the disk was measured as follows:

The disk was placed on a fibrin membrane which had been prepared by adding a physiological saline solution of thrombin and allowed to stand at 37° C. for 24 hours. It was observed that the fibrin membrane was dissolved in a circular form having a diameter of 26 mm around the disk.

EXAMPLE 2

The procedure of Example 1 was repeated with the exception that streptokinase was used in place of urokinase. The disk with streptokinase bonded thereto dissolved the fibrin membrane in a circular form having a diameter of 15 mm.

EXAMPLE 3

A benzene solution of 0.5 (W/V)% of a maleic anhydride-styrene copolymer and 0.1 (W/V)% of polyethylene glycol having a molecular weight of 400 was placed in a nylon-6 tube of an inner diameter of 3 mm, an outer diameter of 5 mm and a length of 35 mm, and allowed to stand at room temperature for 30 minutes. Thereafter, the benzene solution was withdrawn from the tube, and the tube was heated at from 100° C. to 105° C. for 1 hour; this procedure was further repeated three times.

A mixture of 5 mg (5,100 unit) of β-amylase and 1 to 5 mg of reduced glutathion was dissolved in 5 ml of a 1/15 M phosphoric acid buffer solution (pH 6.0). The solution so obtained was injected into the nylon tube and allowed to stand at 7° C. for 24 hours. Thereafter, the nylon tube was washed with a physiological saline solution.

In the nylon-6 tube with β-amylase bonded thereto as described above was injected 1 ml of a 1% soluble starch solution (0.1 M-an acetic acid buffer solution, pH 4.8), and immediately after the injection of the solution, both ends of the nylon tube were connected to form a loop. This loop was placed on a rotating carriage which was canted down by 23° and rotated at a rate of 16 rpm. During this rotation, the temperature was maintained at 25° C. After 5 minutes, the reaction solution was withdrawn and the amount of maltose formed was measured and found to be 4.1 mg (yield 41%).

EXAMPLE 4

A surgical drain (inner diameter 8 mm, outer diameter 10 mm, length 50 cm) for use in thoracic surgery was soaked in an acetone solution of 0.2 (W/V)% of a maleic anhydride-methyl vinyl ether copolymer and 0.2 (W/V)% of diethylene glycol for 30 seconds and then heated under reduced pressure at about 100° C. for 1 hour. This process was conducted one more time.

This drain tube was soaked in a physiological saline solution (1,200 units/ml) of urokinase, allowed to stand at 7° C. for 2 days and then washed with a physiological saline solution. The drain tube with urokinase fixed thereon was cut to a thickness of 2 mm. With the thus-obtained test piece, the fibrinolytic activity was measured using a fibrin plate in the same manner as in Example 1, and it was observed that the fibrin membrane was dissolved in a circular form of a diameter of 24 mm around the test piece.

EXAMPLE 5

The interior of a heart assist device made from polyurethane was filled with an acetone solution of 0.2 (W/V)% of a maleic anhydride-methyl vinyl ether copolymer and 0.4 (W/V)% of polyethylene glycol having a molecular weight of 400, and after allowing to stand for 1 minute, the acetone solution was withdrawn. Thereafter, the heart assist device was heated under reduced pressure at about 100° C. for 1 hour; this process was repeated three more times.

The heart assist device was filled with a physiological saline solution (1,200 units/ml) of urokinase, allowed to stand at 7° C. for 2 days and then washed with a physiological saline solution. The heart assist device with urokinase fixed thereon was cut to a square of 5 mm×5 mm. With this test piece, the fibrinolytic activity was measured using a fibrin plate in the same manner as in Example 1, and it was observed that the fibrin membrane was dissolved in a circular form of a diameter of 32 mm around the test piece.

While the invention has been described in detail and with reference to specific embodiments thereof, it will be apparent to one skilled in the art that various changes and modifications can be made therein without departing from the spirit and scope thereof.

What is claimed is:

1. A process for providing enzyme activity to the surface of an article comprised of an organic polymeric material, comprising forming a film on the surface of the article, said film consisting essentially of an acid anhydride group-containing polymer selected from the group consisting of a maleic anhydride-styrene copolymer, a maleic anhydride-methyl vinyl ether copolymer, and a maleic anhydride-isobutylene copolymer and a polyol, wherein the acid anhydride groups are partially reacted with the polyol, and thereafter reacting the unreacted acid anhydridge group with a fibrinolytic enzyme selected from the group consisting of urokinase or streptokinase.

2. A process as in claim 1, wherein the polyol is diethylene glycol.

3. A process as in claim 1, wherein the polyol is pentaerythritol.

4. A process as in claim 1, wherein the polyol is polyether-polyol.

5. A process as in claim 4 wherein the polyether-polyol is polyethylene glycol.

6. A process as in claim 1, wherein the polyol is a polyester-polyol.

7. A process as in claim 1 wherein the thickness of the film is from about $0.01\mu$ to $500\mu$.

8. A process as in claim 1 wherein the article is made from polyvinyl chloride.

9. A process as in claim 1 wherein the article is made from silicone rubber.

10. A process as in claim 1 wherein the article is made from polyurethane.

11. A process as in claim 1 wherein the article is a tube.

12. A process as in claim 11 wherein the tube is a catheter.

13. A process as in claim 11 wherein the tube is a surgical drain.

14. A process as in claim 11 wherein the tube is a tube for extracorporeal circulation.

15. A process as in claim 11 wherein the tube is a vascular prosthesis.

16. A process as in claim 1 wherein the article is an adsorbent for blood purification.

17. A process as in claim 1 wherein the article is a heart assist device.

18. A process as in claim 1 wherein the article is an artificial heart.

19. A process as in claim 1 wherein the article is an artificial kidney.

20. A process as in claim 1 wherein the article is an artificial lung.

21. A process as in claim 1 wherein the unreacted acid anhydride groups are reacted with the enzyme by treating the article with an enzyme solution at a temperature from about −20° to 60° C. for period of from about 30 minutes to 7 days at an enzyme concentration of from about 0.0001 to 50 mg/l and a pH of from about 3 to 10.

22. A process as in claim 1 wherein the unreacted acid anhydride groups are reacted with the enzyme by treating the article with an enzyme solution at a temperature from 0° to 40° C. for period of from 1 hour to 3 days at an enzyme concentration of from 0.0005 to 10 mg/l and a pH of from 4 to 9.

23. A process as in claim 21 or 22 wherein the solvent for the enzyme solution is selected from the group consisting of water, methanol, ethanol, propanol, dioxane, dimethylformamide, dimethyl sulfoxide, or a mixture thereof.

24. An article comprised of an organic polymeric material having enzyme activity on the surface thereof, said activity being provided by forming a film on the surface of the article, said film consisting essentially of an acid anhydride group-containing polymer selected from the group consisting of a maleic anhydride-styrene copolymer, a maleic anhydride-methyl vinyl ether copolymer, and a maleic anhydride-isobutylene copolymer and a polyol, wherein the acid anhydride groups are partially reacted with the polyol, and thereafter reacting the unreacted acid anhydride groups with a fibrinolytic enzyme selected from the group consisting of urokinase or streptokinase.

25. An article as in claim 24, wherein said article is a tube, an adsorbent for blood purification, a heart assist device, an artificial heart, an artificial kidney, or an artificial lung.

26. An article as in claim 25 wherein the tube is a catheter, a surgical drain, a tube for extracorporeal circulation, or a vascular prosthesis.

* * * * *